US006277819B1

(12) United States Patent
Efendic

(10) Patent No.: US 6,277,819 B1
(45) Date of Patent: *Aug. 21, 2001

(54) USE OF GLP-1 OR ANALOGS IN TREATMENT OF MYOCARDIAL INFARCTION

(75) Inventor: Suad Efendic, Lidingo (SE)

(73) Assignee: Eli Lilly and Company, Indianapolis, IN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/915,918

(22) Filed: Aug. 21, 1997

Related U.S. Application Data

(60) Provisional application No. 60/024,980, filed on Aug. 30, 1996.

(51) Int. Cl.$^7$ ............ A61K 38/26; A61K 38/17; C07K 14/605

(52) U.S. Cl. ................. 514/12; 514/2; 514/866; 530/300

(58) Field of Search .................. 514/2, 12, 866; 530/300

(56) References Cited

U.S. PATENT DOCUMENTS

| | | |
|---|---|---|
| 5,118,666 * | 6/1992 | Habener . |
| 5,120,712 * | 6/1992 | Habener . |
| 5,202,239 | 4/1993 | Hilliker et al. . |
| 5,614,492 * | 3/1997 | Habener . |
| 5,631,224 * | 5/1997 | Efendic et al. . |
| 6,006,753 * | 12/1999 | Efendic . |

FOREIGN PATENT DOCUMENTS

| | | |
|---|---|---|
| 700995 | 3/1996 | (EP) . |
| WO 95/05848 | 3/1995 | (SE) . |
| WO 96/29342 | 9/1996 | (SE) . |
| WO 92/02550 | 2/1992 | (WO) . |

OTHER PUBLICATIONS

Malmberg, et al., "Randomized Trial of Insulin–Glucose Infusion Followed by Subcutaneous Insulin Treatment in Diabetic Patients with Acute Myocardial Infarction (DIGAMI Study): Effects on Mortality at 1 Year" (1995) *JACC*, 26(1):57–65.

Malmberg, et al., "Effects of Insulin Treatment on Cause–Specific One–Year Mortality and Morbidity in Diabetic Patients with Acute Myocardial Infarction" (1996) *European Heart Journal*, 17:1337–1344.

Fava, et al., "The Prognostic Value of Blood Glucose in Diabetic Patients with Acute Myocardial Infarction" (1996) *Diabetic Medicine* 13:80–83.

Oswald, et al., "Determinants and Importance of Stress Hyperglycaemia in Non–Diabetic Patients with Myocardial Infarction" (1986) *British Medical Journal* 293:917–922.

Bellodi, et al., "Hyperglycemia and Prognosis of Acute Myocardial Infarction in Patients Without Diabetes Mellitus" (1989) *The American Journal of Cardiology* 64:885–888.

O'Sullivan, et al., "In–Hospital Prognosis of Patients With Fasting Hyperglycemia After First Myocardial Infarction" (1991) *Diabetes Care* 14 (8):758–760.

Mak, K. H., et al., "Fasting Blood Sugar Level: A Determinant for In–hospital Outcome in Patients with First Myocardial infarction and Without Glucose Intolerance" (1993) *Annals Academy of Medicine*, 22(3):291–295.

Araki, et al. (1992) *Journal of Cerebral Blood Flow and Metabolism* 12:469–476.

Barbash, et al. (1993) *JACC* 22(3):707–13.

Bell (1994) *Diabetes Care* 17(3):213–219.

Broderick, et al. (1995) *Stroke* 26:484–487.

Derouesné, et al. (1993) *Acta. Neurol. Scand.* 87:361–366.

Chukwuma, et al. (1993) *J. Diab. Comp.* 7:250–262.

Davì, et al. (1990) *The New England Journal of Medicine* 322(25):1769–74.

Dhanvantari, et al. (1996) *Molecular Endocrinology* 10:342–355.

Dietrich, et al. (1993) *Stroke* 24:111–116.

Dimlich, et al. (1992) *Stroke* 23:1145–1153.

De Falco, et al. (1993) *Schweizer Archiv für Neurologie und Psychiatric Band* 144(3):233–239.

Fang, et al. (1995) *Chinese Med J.* 108(4):259–261.

Fehmann, et al. (1992) *Molecular and Cellular Endocrinology* 85:C39–C44.

Granger, et al. (1993) *American College of Cardiology* 21(4):920–925.

Grines, et al. (1993) *The New England Journal of Medicine* 328(10):673–679.

Gundersen, et al. (1983) *Diabetes Care* 6(3):285–290.

Hamann, et al. (1996) *Exp. Clin. Endocrinol.& Diabetes* 104:293–300.

Hamsten (1994) *J. of Int. Med.* 236:736–1–3.

Janghorbani, et al. (1994) *J. Clin. Epidemiol.* 47(4):397–405.

Karlson, et al. (1993) *Diabetic Medicine* 10:449–454.

Kiers, et al. (1992) *J. Neurol., Neurosurg., and Psych.* 55:263–270.

Kittaka, et al. (1996) *Stroke* 27:712–719.

Van Kooten, et al. (1993) *Stroke* 24:1129–1132.

Fibrinolytic Therapy Trialists' (FTT) Collaborative Group (1994) *The Lancet* 343:311–322.

Lehto, et al. (1996) *Stroke* 27:63–68.

(List continued on next page.)

Primary Examiner—Christine J. Saoud
(74) Attorney, Agent, or Firm—Mark J. Stewart; James J. Kelley

(57) ABSTRACT

This invention provides a method of reducing mortality and morbidity after myocardial infarction. GLP-1, a GLP-1 analog, or a GLP-1 derivative, is administered at a dose effective to normalize blood glucose.

19 Claims, 2 Drawing Sheets

OTHER PUBLICATIONS

Malmberg, et al. (1988) *European Heart Journal* 9:259–264.
Malmberg, et al. (1989) *European Heart Journal* 10:423–428.
Wass, et al. (1996) *Mayo Clin. Proc.* 71:801–812.
Wheeler, et al. (1993) *Endocinology* 133(1):57–62.
Wingard, et al. (1993) *Diabetes Care* 16(7):1022–1025.
Wolffenbuttel, et al. (1995) *Drugs* 50(2):263–288.
Lowenthal, *Geriatric Cardiology*, Chap. 2 in Cardiovascular Clinics, Brest, A.N. ed., F.A. Davis Company.

* cited by examiner

USE OF GLP-1 OR ANALOGS IN TREATMENT OF MYOCARDIAL INFARCTION

This application claims the benefit of U.S. Provisional Application Ser. No. 60/024,980, filed Aug. 30, 1996.

BACKGROUND OF THE INVENTION

1. Field of the Invention

This invention relates to a method of reducing mortality and morbidity after myocardial infarction in diabetic patients.

2. Background Information

Morbidity and mortality from cardiovascular disease is higher in patients with manifest diabetes or impaired glucose tolerance compared to patients without those disorders. Diabetics account for up to 24% of the total number of patients admitted to coronary care units for suspect infarction, whereas they constitute only about 5% of the general population [Malmberg and Rydén; Fuller J. H., *Diabet. Metab.* 19:96–99 (1993)]. In-hospital. mortality of diabetic patients with myocardial infarction is twice that of non-diabetics [Hamsten A., et al., *J. Int. Med.* 736:1–3 (1994) 236 Suppl.; Malmberg K. and Rydén L., *Eur. Heart J.* 9:256–264 (1988)]. Diabetics experience more morbidity and die more often in the post-acute recovery phase, mostly due to fatal re-infarction and congestive heart failure [Malmberg and Rydén; Stone P., et al., *J. Am. Coll. Cardiol.* 14:49–57 (1989); Karlson B. W., et al., *Diabet. Med.* 10(5):449–54 (1993); Barbash G. I., et al., *J. Am. Coll. Cardiol.* 22:707–713 (1993)]. The difference in mortality and morbidity between diabetics and non-diabetics following myocardial infarction persists, despite reduction in the incidence of morbidity and mortality following acute myocardial infarction [Granger C. B., et al., *J. Am. Coll. Cardiol.*, 21(4):920–5 (1993); Grines C., et al., *N. Engl. J. Med.* 328:673–679 (1993)].

Factors responsible for the poor prognosis among diabetic patients with acute myocardial infarction may act before, during, or after the acute event. They include diffuse coronary atheromatosis, with more advanced and widespread coronary artery disease, which, together with a possible diabetic cardiomyopathy, may contribute to a high prevalence of congestive heart failure. Autonomic neuropathy with impaired pain perception and increased resting heart rate variability may also be of importance. A coronary thrombus is an essential part of an evolving infarction, and notably, platelet activity, coagulation, and fibrinolytic functions have been found to be disturbed in diabetic patients [Davi G., et al., *New England. J. Med.*, 322:1769–1774 (1990)].

Exaggerated metabolic disturbances in diabetics may play an important role. Myocardial infarction causes a reduction in circulating insulin, a dramatic increase in adrenergic tone, and the release of stress hormones, such as, cortisone, catecholamines, and glucagon, that together enhance hyperglycemia and stimulate lipolysis. The released free fatty acids further injure the myocardium via several mechanisms, and excessive oxidation of free fatty acids may possibly damage nonischemic parts of the myocardium [Rodrigues B., et al., *Cardiovascular Research*, 26(10):913–922 (1992)].

Palliative measures to normalize blood glucose and to control the metabolic cascade that exacerbates infarct damage in diabetics are needed. In a recent trial, improved metabolic care of diabetic patients during acute myocardial infarction, including carefully-monitored infusion of insulin and glucose, and post-acute tight regulation of blood glucose by subcutaneous multidose insulin treatment lowered mortality during the year following myocardial infarction by 30% compared with a control group of diabetics who did not receive insulin treatment unless deemed clinically necessary [Malmberg, K, et al., *J. Am. College Cardiology*, 26:57–65 (1995)].

Insulin infusion, however, creates the potential for hypoglycemia, which is defined as blood glucose below 0.3 mM. Hypoglycemia increases the risk of ventricular arrhythmia and is a dangerous consequence of insulin infusion. An algorithm for insulin infusion for diabetics with myocardial infarction was developed to prevent hypoglycemia [Hendra, T. J., et al., *Diabetes Res. Clin. Pract.*, 16:213–220 (1992)]. However, 21% of the patients developed hypoglycemia under this algorithm. In another study of glucose control following myocardial infarction, 18% of the patients developed hypoglycemia when infused with insulin and glucose [Malmberg, K. A., et al., *Diabetes Care*, 17:1007–1014 (1994)].

Insulin infusion also requires frequent monitoring of blood glucose levels so that the onset of hypoglycemia can be detected and remedied as soon as possible. In patients receiving insulin infusion in the cited study [Malmberg, 1994], blood glucose was measured at least every second hour, and the rate of infusion adjusted accordingly. Thus, the safety and efficacy of insulin-glucose infusion therapy for myocardial infarct patients depends on easy and rapid access to blood glucose data. Such an intense need for monitoring blood glucose places a heavy burden on health care professionals, and increases the inconvenience and cost of treatment. As a result, cardiac intensive care units often do not allot resources for optimizing blood glucose levels in diabetics with acute myocardial infarction, as might be obtained by intravenous administration of insulin. Considering the risks and burdens inherent in insulin infusion, an alternate approach to management of blood glucose during acute myocardial infarction in diabetics is needed.

The incretin hormone, glucagon-like peptide 1, abbreviated as GLP-1, is processed from proglucagon in the gut and enhances nutrient-induced insulin release [Krcymann B., et al., *Lancet* 2:1300–1303 (1987)]. Various truncated forms of GLP-1, are known to stimulate insulin secretion (insulinotropic action) and cAMP formation [see, e g., Mojsov, S., *Int. J. Peptide Protein Research*, 40:333–343 (1992)]. A relationship between various in vitro laboratory experiments and mammalian, especially human, insulinotropic responses to exogenous administration of GLP-1, GLP-1(7-36) amide, and GLP-1(7-37) acid has been established [see, e.g., Nauck, M. A., et al., *Diabetologia*, 36:741–744 (1993); Gutniak, M., et al., *New England J. of Medicine*, 326(20):1316–1322 (1992); Nauck, M. A., et al., *J. Clin. Invest.*, 91:301–307 (1993); and Thorens, B., et al., *Diabetes*, 42:1219–1225 (1993)]. GLP-1(7-36) amide exerts a pronounced antidiabetogenic effect in insulin-dependent diabetics by stimulating insulin sensitivity and by enhancing glucose-induced insulin release at physiological concentrations [Gutniak M., et al., *New England J. Med.* 326:1316–1322 (1992)]. When administered to non-insulin dependent diabetics, GLP-1(7-36) amide stimulates insulin release, lowers glucagon secretion, inhibits gastric emptying and enhances glucose utilization [Nauck, 1993; Gutniak, 1992; Nauck, 1993].

The use of GLP-1 type molecules for prolonged therapy of diabetes has been obstructed because the serum half-life of such peptides is quite short. For example, GLP-1(7-37)

has a serum half-life of only 3 to 5 minutes. GLP-1(7-36) amide has a half-life of about 50 minutes when administered subcutaneously. Thus, these GLP molecules must be administered as a continuous infusion to achieve a prolonged effect [Gutniak M., et al., *Diabetes Care* 17:1039–1044 (1994)]. In the present invention, GLP-1's short half-life and the consequent need for continuous administration are not disadvantages because the patient is typically bed-ridden, in a cardiac intensive care unit, where fluids are continuously administered parenterally.

SUMMARY OF THE INVENTION

The present invention provides a method of reducing mortality and morbidity after myocardial infarction, comprising administering a compound from the group consisting of GLP-1, GLP-1 analogs, GLP-1 derivatives, and pharmaceutically-acceptable salts thereof, at a dose effective to normalize blood glucose, to a patient in need thereof.

The present invention provides the benefits of reduction in mortality and morbidity after myocardial infarction observed in combined treatment with glucose and insulin in diabetics during acute myocardial infarction, but without the inconvenient and expensive requirement of frequent monitoring of blood glucose, interpretation of blood glucose results, and adjustment of insulin dose rate, and without the ever-present risk of hypoglycemia that accompanies insulin infusion.

DETAILED DESCRIPTION OF THE INVENTION

Figure 1:
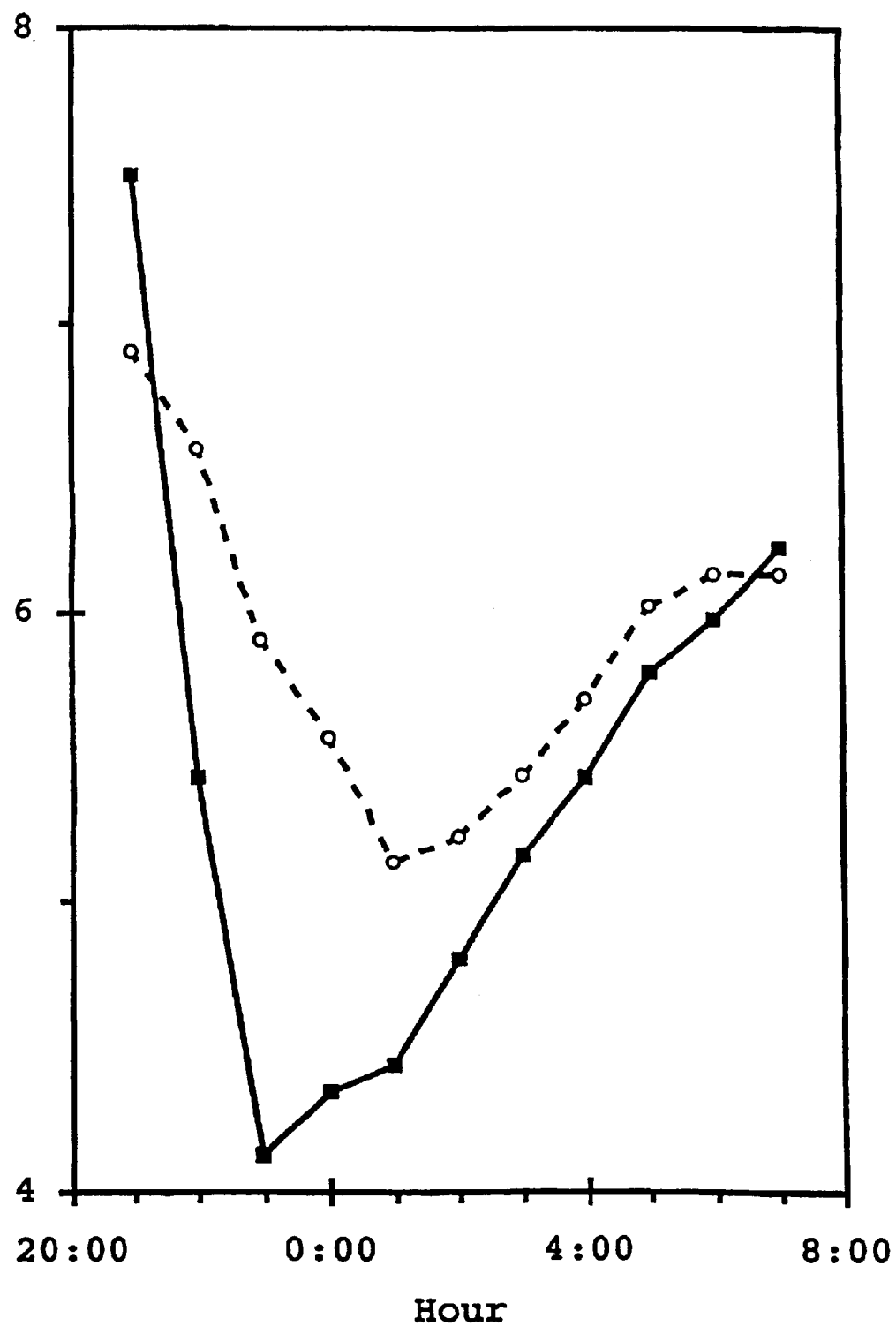
FIG. 1 is a graph showing the effect of continuous infusion GLP-1 (7-36) amide on average blood glucose concentration (mM) —■— in five NIDDM patients during the night. The graph also depicts the effect of continuous insulin infusion on average blood glucose concentration --O-- in the same five NIDDM patients, but on a different night.

"GLP-1" means GLP-1(7-37). By custom in the art, the amino-terminus of GLP-1(7-37) has been assigned number 7 and the carboxy-terminus, number 37. The amino acid sequence of GLP-1(7-37) is well-known in the art, but is presented below for the reader's convenience:

(SEQ ID NO:1)
$NH_2$-His$^7$-Ala-Glu-Gly$^{10}$-

Thr-Phe-Thr-Ser-Asp$^{15}$-Val-Ser-Ser-Tyr-Leu$^{20}$-

Glu-Gly-Gln-Ala-Ala$^{25}$-Lys-Glu-Phe-Ile-Ala$^{30}$-

Trp-Leu-Val-Lys-Gly$^{35}$-Arg-Gly$^{37}$-COOH

A "GLP-1 analog" is defined as a molecule having one or more amino acid substitutions, deletions, inversions, or additions compared with GLP-1. GLP-1 analogs known in the art include, for example, GLP-1(7-34) and GLP-1(7-35), GLP-1(7-36), Gln$^9$-GLP-1(7-37), D-Gln$^9$-GLP-1(7-37), Thr$^{16}$-Lys$^{18}$-GLP-1(7-37), and Lys$^{18}$-GLP-1(7-37). Preferred GLP-1 analogs are GLP-1(7-34) and GLP-1(7-35), which are disclosed in U.S. Pat. No: 5,118,666, herein incorporated by reference, and also GLP-1(7-36), which are the biologically processed forms of GLP-1 having insulinotropic properties. Other GLP-1 analogs are disclosed in U.S. Pat. No. 5,545,618 which is incorporated herein by reference.

A "GLP-1 derivative" is defined as a molecule having the amino acid sequence of GLP-1 or of a GLP-1 analog, but additionally having chemical modification of one or more of its amino acid side groups, α-carbon atoms, terminal amino group, or terminal carboxylic acid group. A chemical modification includes, but is not limited to, adding chemical moieties, creating new bonds, and removing chemical moieties. Modifications at amino acid side groups include, without limitation, acylation of lysine ε-amino groups, N-alkylation of arginine, histidine, or lysine, alkylation of glutamic or aspartic carboxylic acid groups, and deamidation of glutamine or asparagine. Modifications of the terminal amino include, without limitation, the des-amino, N-lower alkyl, N-di-lower alkyl, and N-acyl modifications. Modifications of the terminal carboxy group include, without limitation, the amide, lower alkyl amide, dialkyl amide, and lower alkyl ester modifications. Lower alkyl is $C_1$-$C_4$ alkyl. Furthermore, one or more side groups, or terminal groups, may be protected by protective groups known to the ordinarily-skilled protein chemist. The α-carbon of an amino acid may be mono- or SEQ ID NO: 6 dimethylated.

A preferred group of GLP-1 analogs and derivatives for use in the present invention is composed of molecules of the formula:

(SEQ ID NO:2)
$R_1$-X-Glu-Gly$^{10}$-

Thr-Phe-Thr-Ser-Asp$^{15}$-Val-Ser-Ser-Tyr-Leu$^{20}$-

Y -Gly-Gln-Ala-Ala$^{25}$-Lys- Z -Phe-Ile-Ala$^{30}$-

Trp-Leu-Val-Lys-Gly$^{35}$-Arg-$R_2$ and pharmaceutically-acceptable salts thereof, wherein: $R_1$ is selected from the group consisting of L-histidine, D-histidine, desamino-histidine, 2-amino-histidine, β-hydroxy-histidine, homohistidine, alpha-fluoromethyl-histidine, and alpha-methyl-histidine; X is selected from the group consisting of Ala, Gly, Val, Thr, Ile, and alpha-methyl-Ala; Y is selected from the group consisting of Glu, Gln, Ala, Thr, Ser, and Gly; Z is selected from the group consisting of Glu, Gln, Ala, Thr, Ser, and Gly; and $R_2$ is selected from the group consisting of $NH_2$, and Gly—OH; provided that the compound has an isoelectric point in the range from about 6.0 to about 9.0 and further providing that when $R_1$ is His, X is Ala, Y is Glu, and Z is Glu, $R_2$ must be $NH_2$.

Numerous GLP-1 analogs and derivatives having an isoelectric point in this range have been disclosed and include, for example:

GLP-1 (7-36)$NH_2$

Gly$^8$-GLP-1 (7-36)$NH_2$

Gln$^9$-GLP-1 (7-37)

-continued

D-Gln$^9$-GLP-1 (7-37)

acetyl-Lys$^9$-GLP-1 (7-37)

Thr$^9$-GLP-1 (7-37)

D-Thr$^9$-GLP-1 (7-37)

Asn$^9$-GLP-1 (7-37)

D-Asn$^9$-GLP-1 (7-37)

Ser$^{22}$-Arg$^{23}$-Arg$^{24}$-Gln$^{26}$-GLP-1 (7-37)    SEQ ID NO:6

Thr$^{16}$-Lys$^{18}$-GLP-1 (7-37)

Lys$^{18}$-GLP-1 (7-37)

Arg$^{23}$-GLP-1 (7-37)

Arg$^{24}$-GLP-1 (7-37), and the like
[see, e.g., WO 91/11457].

Another preferred group of active compounds for use in the present invention is disclosed in WO 91/11457, and consists essentially of GLP-1(7-34), GLP-1(7-35), GLP-1 (7-36), or GLP-1(7-37), or the amide form thereof, and pharmaceutically-acceptable salts thereof, having at least one modification selected from the group consisting of:

(a) substitution of glycine, serine, cysteine, threonine, asparagine, glutamine, tyrosine, alanine, valine, isoleucine, leucine, methionine, phenylalanine, arginine, or D-lysine for lysine at position 26 and/or position 34; or substitution of glycine, serine, cysteine, threonine, asparagine, glutamine, tyrosine, alanine, valine, isoleucine, leucine, methionine, phenylalanine, lysine, or a D-arginine for arginine at position 36;

(b) substitution of an oxidation-resistant amino acid for tryptophan at position 31;

(c) substitution of at least one of: tyrosine for valine at position 16; lysine for serine at position 18; aspartic acid for glutamic acid at position 21; serine for glycine at position 22; arginine for glutamine at position 23; arginine for alanine at position 24; and glutamine for lysine at position 26; and (d) substitution of at least one of: glycine, serine, or cysteine for alanine at position 8; aspartic acid, glycine, serine, cysteine, threonine, asparagine, glutamine, tyrosine, alanine, valine, isoleucine, leucine, methionine, or phenylalanine for glutamic acid at position 9; serine, cysteine, threonine, asparagine, glutamine, tyrosine, alanine, valine, isoleucine, leucine, methionine, or phenylalanine for glycine at position 10; and glutamic acid for aspartic acid at position 15; and (e) substitution of glycine, serine, cysteine, threonine, asparagine, glutamine, tyrosine, alanine, valine, isoleucine, leucine, methionine, or phenylalanine, or the D- or N-acylated or alkylated form of histidine for histidine at position 7; wherein, in the substitutions is (a), (b), (d), and (e), the substituted amino acids can optionally be in the D-form and the amino acids substituted at position 7 can optionally be in the N-acylated or N-alkylated form.

Because the enzyme, dipeptidyl-peptidase IV (DPP IV), may be responsible for the observed rapid in vivo inactivation of administered GLP-1, [see, e.g., Mentlein, R., et al., Eur. J. Biochem., 214:829–835 (1993)], administration of GLP-1 analogs and derivatives that are protected from the activity of DPP IV is preferred, and the administration of Gly$^8$-GLP-1(7-36)NH$_2$, Val$^8$-GLP-1(7-37)OH, a-methyl-Ala$^8$-GLP-1(7-36)NH$_2$, and Gly$^8$-Gln$^{21}$-GLP-1(7-37)OH, or pharmaceutically-acceptable salts thereof, is more preferred.

The use in the present invention of a molecule claimed in U.S. Pat. No. 5,188,666, which is expressly incorporated by reference, is preferred. Such molecule is selected from the group consisting of a peptide having the amino acid sequence:

(SEQ ID NO:3)
NH$_2$-His$^7$-Ala-Glu-Gly$^{10}$-

Thr-Phe-Thr-Ser-Asp$^{15}$-Val-Ser-Ser-Tyr-Leu$^{20}$-

Glu-Gly-Gln-Ala-Ala$^{25}$-Lys-Glu-Phe-Ile-Ala$^{30}$-

Trp-Leu-Val-X wherein X is selected from the group consisting of Lys and Lys—Gly; and a derivative of said peptide, wherein said peptide is selected from the group consisting of: a pharmaceutically-acceptable acid addition salt of said peptide; a pharmaceutically-acceptable carboxylate salt of said peptide; a pharmaceutically-acceptable lower alkylester of said peptide; and a pharmaceutically-acceptable amide of said peptide selected from the group consisting of amide, lower alkyl amide, and lower dialkyl amide.

Another preferred group of molecules for use in the present invention consists of compounds, claimed in U.S. Pat. No. 5,512,549, which is expressly incorporated herein by reference, of the general formula:

(SEQ ID NO:4)
R$^1$-Ala-Glu-Gly$^{10}$-
Thr-Phe-Thr-Ser-Asp$^{15}$-Val-Ser-Ser-Tyr-Leu$^{20}$-
Glu-Gly-Gln-Ala-Ala$^{25}$-Xaa-Glu-Phe-Ile-Ala$^{30}$-
Trp-Leu-Val-Lys$^{35}$-Arg-R$^3$
|
R$^2$ and pharmaceutically-acceptable salts thereof, wherein R$^1$ is selected from the group consisting of 4-imidazopropionyl, 4-imidazoacetyl, or 4-imidazo-α,α dimethyl-acetyl; R$^2$ is selected from the group consisting of C$_6$–C$_{10}$ unbranched acyl, or is absent; R$^3$ is selected from the group consisting of Gly—OH or NH$_2$; and, Xaa is Lys or Arg, may be used in present invention.

More preferred compounds of SEQ ID NO:4 for use in the present invention are those in which Xaa is Arg and R$^2$ is C$_6$–C$_{10}$ unbranched acyl.

Highly preferred compounds of SEQ ID NO:4 for use in the present invention are those in which Xaa is Arg, R$^2$ is C$_6$–C$_{10}$ unbranched acyl, and R$^3$ is Gly—OH.

More highly preferred compounds of SEQ ID NO:4 for use in the present invention are those in which Xaa is Arg, R$^2$ is C$_6$–C$_{10}$ unbranched acyl, R$^3$ is Gly—OH, and R$^1$ is 4-imidazopropionyl.

The most preferred compound of SEQ ID NO:4 for use in the present invention is that in which Xaa is Arg, R$^2$ is C$_8$ unbranched acyl, R$^3$ is Gly—OH, and R$^1$ is 4-imidazopropionyl.

The use in the present invention of a molecule claimed in U.S. Pat. No. 5,120,712, which is expressly incorporated by reference, is highly preferred. Such molecule is selected from the group consisting of a peptide having the amino acid sequence:

(SEQ ID NO:1)
NH$_2$-His$^7$-Ala-Glu-Gly$^{10}$-

Thr-Phe-Thr-Ser-Asp$^{15}$-Val-Ser-Ser-Tyr-Leu$^{20}$-

Glu-Gly-Gln-Ala-Ala$^{25}$-Lys-Glu-Phe-Ile-Ala$^{30}$-

Trp-Leu-Val-Lys-Gly$^{35}$-Arg-Gly$^{37}$-COOH and a derivative of said peptide, wherein said peptide is selected from the group consisting of: a pharmaceutically-acceptable acid addition salt of said peptide; a pharmaceutically-acceptable carboxylate salt of said peptide; a pharmaceutically-acceptable lower alkylester of said peptide; and a pharmaceutically-acceptable amide of said peptide selected from the group consisting of amide, lower alkyl amide, and lower dialkyl amide.

The use of GLP-1(7-36) amide, or a pharmaceutically-acceptable salt thereof, in the present invention is most highly preferred. The amino acid sequence of GLP-1(7-36) amide is:

(SEQ ID NO:5)
NH$_2$-His$^7$-Ala-Glu-Gly$^{10}$-

Thr-Phe-Thr-Ser-Asp$^{15}$-Val-Ser-Ser-Tyr-Leu$^{20}$-

Glu-Gly-Gln-Ala-Ala$^{25}$-Lys-Glu-Phe-Ile-Ala$^{30}$-

Trp-Leu-Val-Lys-Gly$^{35}$-Arg-NH$_2$

Methods for preparing the active compound used in the present invention, namely, GLP-1, an GLP-1 analog, or a GLP-1 derivative used in the present invention are well-known, and are described in U.S. Pat. Nos. 5,118,666, 5,120,712, and 5,523,549, which are incorporated by reference.

The amino acid portion of the active compound used in the present invention, or a precursor thereto, is made either by 1) solid-phase synthetic chemistry; 2) purification of GLP molecules from natural sources; or 3) recombinant DNA technology.

Solid phase chemical synthesis of polypeptides is well known in the art and may be found in general texts in the area such as Dugas, H. and Penney, C., *Bioorganic Chemistry,* Springer-Verlag, New York (1981), pp. 54–92, Merrifield, J. M., *Chem. Soc.,* 85:2149 (1962), and Stewart and Young, *Solid Phase Peptide Synthesis,* Freeman, San Francisco (1969) pp. 24–66.

For example, the amino acid portion may be synthesized by solid-phase methodology utilizing a 430A peptide synthesizer (PE-Applied Biosystems, Inc., 850 Lincoln Center Drive, Foster City, Calif. 94404) and synthesis cycles supplied by PE-Applied Biosystems. BOC-amino acids and other reagents are commercially available from PE-Applied Biosystems and other chemical supply houses. Sequential Boc chemistry using double couple protocols are applied to the starting p-methyl benzhydryl amine resins for the production of C-terminal carboxamides. For the production of C-terminal acids, the corresponding PAM resin is used. Asn, Gln, and Arg are coupled using preformed hydroxy benzotriazole esters. The following side chain protecting groups may be used:
Arg, Tosyl
Asp, cyclohexyl
Glu, cyclohexyl
Ser, Benzyl
Thr, Benzyl
Tyr, 4-bromo carbobenzoxy Boc deprotection may be accomplished with trifluoroacetic acid in methylene chloride. Following completion of the synthesis the peptides may be deprotected and cleaved from the resin with anhydrous hydrogen fluoride (HF) containing 10% meta-cresol. Cleavage of the side chain protecting group(s) and of the peptide from the resin is carried out at −5° C. to 5° C., preferably on ice for 60 minutes. After removal of the HF, the peptide/resin is washed with ether, and the peptide extracted with glacial acetic acid and lyophilized.

Techniques well-known to the ordinarily-skilled artisan in recombinant DNA technology may be used to prepare the active compound used in present invention. In fact, recombinant DNA methods may be preferable because of higher yield. The basic steps in recombinant production are:

a) isolating a natural DNA sequence encoding a GLP-1 molecule or constructing a synthetic or semi-synthetic DNA coding sequence for a GLP-1 molecule, b) placing the coding sequence into an expression vector in a manner suitable for expressing proteins either alone or as a fusion proteins, c) transforming an appropriate eukaryotic or prokaryotic host cell with the expression vector, d) culturing the transformed host cell under conditions that will permit expression of a GLP-1 molecule, and e) recovering and purifying the recombinantly produced GLP-1 molecule.

As previously stated, the coding sequences may be wholly synthetic or the result of modifications to the larger, native glucagon-encoding DNA. A DNA sequence that encodes preproglucagon is presented in Lund, et al., *Proc. Natl. Acad. Sci. U.S.A.* 79:345–349 (1982) and may be used as starting material in the semisynthetic production of the compounds of the present invention by altering the native sequence to achieve the desired results.

Synthetic genes, the in vitro or in vivo transcription and translation of which results in the production of a GLP-1 molecule, may be constructed by techniques well known in the art. Owing to the natural degeneracy of the genetic code, the skilled artisan will recognize that a sizable yet definite number of DNA sequences may be constructed, all of which encode GLP-1 molecules.

The methodology of synthetic gene construction is well-known in the art. See Brown, et al. (1979) *Methods in Enzymology,* Academic Press, N.Y., Vol. 68, pgs. 109–151. The DNA sequence is designed from the desired amino acid sequence using the genetic code, which is easily ascertained by the ordinarily-skilled biologist. Once designed, the sequence itself may be generated using conventional DNA synthesizing apparatus such as the Model 380A or 380B DNA synthesizers (PE-Applied Biosystems, Inc., 850 Lincoln Center Drive, Foster City, Calif. 94404).

To express the amino acid portion of a compound used in the present invention, one inserts the engineered synthetic DNA sequence in any one of many appropriate recombinant DNA expression vectors through the use of appropriate restriction endonucleases. See generally Maniatis et al. (1989) *Molecular Cloning; A Laboratory Manual,* Cold Springs Harbor Laboratory Press, N.Y., Vol. 1–3. Restriction endonuclease cleavage sites are engineered into either end of the GLP-1 molecule-encoding DNA to facilitate isolation from, and integration into, amplification and expression vectors well-known in the art. The particular endonucleases employed will be dictated by the restriction endonuclease cleavage pattern of the parent expression vector employed. Restriction sites are chosen to properly orient the coding sequence with control sequences, thereby achieving proper in-frame reading and expression of the protein of interest. The coding sequence must be positioned to be in proper reading frame with the promoter and ribosome binding site of the expression vector, both of which are functional in the host cell in which the protein is to be expressed.

To achieve efficient transcription of the synthetic gene, it must be operably associated with a promoter-operator region. Therefore, the promoter-operator region of the synthetic gene is placed in the same sequential orientation with respect to the ATG start codon of the synthetic gene.

A variety of expression vectors useful for transforming prokaryotic and eukaryotic cells are well known in the art. See *The Promega Biological Research Products Catalogue* (1992) (Promega Corp., 2800 Woods Hollow Road, Madison, Wis., 53711–5399); and *The Stratagene Cloning Systems Catalogue* (1992) (Stratagene Corp., 11011 North Torrey Pines Road, La Jolla, Calif., 92037). Also, U.S. Pat. No. 4,710,473 describes circular DNA plasmid transformation vectors useful for expression of exogenous genes in *E. coli* at high levels. These plasmids are useful as transformation vectors in recombinant DNA procedures and (a) confer on the plasmid the capacity for autonomous replication in a host cell;
(b) control autonomous plasmid replication in relation to the temperature at which host cell cultures are maintained;
(c) stabilize maintenance of the plasmid in host cell populations;
(d) direct synthesis of a protein product indicative of plasmid maintenance in a host cell population;
(e) provide in-series restriction endonuclease recognition sites unique to the plasmid; and
(f) terminate mRNA transcription.

These circular DNA plasmids are useful as vectors in recombinant DNA procedures for securing high levels of expression of exogenous genes.

Having constructed an expression vector for the amino acid portion of a compound used in the present invention, the next step is to place the vector into a suitable cell and thereby construct a recombinant host cell useful for expressing the polypeptide. Techniques for transforming cells with recombinant DNA vectors are well known in the art and may be found in such general references as Maniatis, et al. supra. Host cells made be constructed from either eukaryotic or prokaryotic cells.

Prokaryotic host cells generally produce the protein at higher rates and are easier to culture. Proteins expressed in high-level bacterial expression systems characteristically aggregate in granules or inclusion bodies, which contain high levels of the overexpressed protein. Such protein aggregates typically must be recovered, solubilized, denatured and refolded using techniques well known in the art. See Kreuger, et al. (1990) in *Protein Folding,* Gierasch and King, eds., pgs 136–142, American Association for the Advancement of Science Publication No. 89-18S, Washington, D.C.; and U.S. Pat. No. 4,923,967.

Alterations to a precursor GLP-1 or GLP-1 analog amino acid sequence, to produce a desired GLP-1 analog or GLP-1 derivative, are made by well-known methods: chemical modification, enzymatic modification, or a combination of chemical and enzymatic modification of GLP-1 precursors. The techniques of classical solution phase methods and semi-synthetic methods may also be useful for preparing the GLP-1 molecules used in the present invention. Methods for preparing the GLP-1 molecules of the present invention are well known to an ordinarily skilled peptide chemist.

Addition of an acyl group to the epsilon amino group of $Lys^{34}$ may be accomplished using any one of a variety of methods known in the art. See *Bioconjugate Chem.* "Chemical Modifications of Proteins: History and Applications" pages 1, 2–12 (1990) and Hashimoto et al., *Pharmaceutical Res.* 6(2):171–176 (1989).

For example, an N-hydroxy-succinimide ester of octanoic acid can be added to the lysyl-epsilon amine using 50% acetonitrile in borate buffer. The peptide can be acylated either before or after the imidazolic group is added. Moreover, if the peptide is prepared recombinantly, acylation prior to enzymatic cleavage is possible. Also, the lysine in the GLP-1 derivative can be acylated as taught in WO96-29342, which is incorporated herein by reference.

The existence and preparation of a multitude of protected, unprotected, and partially-protected, natural and unnatural, functional analogs and derivatives of GLP-1 (7-36)amide and GLP-1 (7-37) molecules have been described in the art [see, e.g., U.S. Pat. No. 5,120,712 and 5,118,666, which are herein incorporated by reference, and Orskov, C., et al., *J. Biol. Chem.*, 264(22):12826–12829 (1989) and WO 91/11457 (Buckley, D. I., et al., published Aug. 8, 1991)].

Optionally, the amino and carboxy terminal amino acid residues of GLP-1 derivatives may be protected, or, optionally, only one of the termini is protected. Reactions for the formation and removal of such protecting groups are described in standard works including, for example, "Protective Groups in Organic Chemistry", Plenum Press, London and New York (1973); Green, T. H., "Protective Groups in Organic Synthesis", Wiley, New York (1981); and "The Peptides", Vol. I, Schröder and Lübke, Academic Press London and New York (1965). Representative amino-protecting groups include, for example, formyl, acetyl, isopropyl, butoxycarbonyl, fluorenylmethoxycarbonyl, carbobenzyloxy, and the like. Representative carboxy-protecting groups include, for example, benzyl ester, methyl ester, ethyl ester, t-butyl ester, p-nitro phenyl ester, and the like.

Carboxy-terminal, lower-alkyl-ester, GLP-1 derivatives used in the present invention are prepared by reacting the desired ($C_1$–$C_4$) alkanol with the desired polypeptide in the presence of a catalytic acid such as hydrochloric acid. Appropriate conditions for such alkyl ester formation include a reaction temperature of about 50° C. and reaction time of about 1 hour to about 3 hours. Similarly, alkyl ester derivatives of the Asp and/or Glu residues can be formed.

Preparation of a carboxamide derivative of a compound used in the present invention is formed, for example, as described in Stewart, J. M., et al., *Solid Phase Peptide Synthesis,* Pierce Chemical Company Press, 1984.

A pharmaceutically-acceptable salt form of GLP-1, of a GLP-1 analog, or of a GLP-1 derivative may be used in the present invention. Acids commonly employed to form acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, and the like. Examples of such salts include the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, methanesulfonate, propanesulfonate, naphthalene-1-sulfonate, naphthalene-2-sulfonate, mandelate, and the like. Preferred acid addition salts are those formed with mineral acids such as hydrochloric acid and hydrobromic acid, and, especially, hydrochloric acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, and the like. The salt forms are particularly preferred.

A GLP-1, GLP-1 analog, or GLP-1 derivative used in the present invention may be formulated with one or more excipients before use in the present invention. For example, the active compound used in the present invention may be complexed with a divalent metal cation by well-known methods. Such metal cations include, for example, $Zn^{++}$, $Mn^{++}$, $Fe^{++}$, $Co^{++}$, $Cd^{++}$, $Ni^{++}$, and the like.

Optionally, the active compound used in the present invention may be combined with a pharmaceutically-acceptable buffer, and the pH adjusted to provide acceptable stability, and a pH acceptable for parenteral administration.

Optionally, one or more pharmaceutically-acceptable anti-microbial agents may be added. Meta-cresol and phenol are preferred pharmaceutically-acceptable anti-microbial agents. One or more pharmaceutically-acceptable salts may be added to adjust the ionic strength or tonicity. One or more excipients may be added to further adjust the isotonicity of the formulation. Glycerin is an example of an isotonity-adjusting excipient.

Administration may be via any route known to be effective by the physician of ordinary skill. Parenteral administration is preferred. Parenteral administration is commonly understood in the medical literature as the injection of a dosage form into the body by a sterile syringe or some other mechanical device such as an infusion pump. Parenteral routes include intravenous, intramuscular, subcutaneous, intraperitoneal, intraspinal, intrathecal, inracerebroventricular, intraarterial, subarachnoid, and epidural. Intravenous, intramuscular, and subcutaneous routes of administration of the compounds used in the present invention are more preferred. Intravenous and subcutaneous routes of administration of the compounds used in the present invention are yet more highly preferred. For parenteral administration, an active compound used in the present invention preferably is combined with distilled water at an appropriate pH.

Additional pharmaceutical methods may be employed to control the duration of action. Controlled release preparations may be achieved by the use of polymers to complex or absorb the active compound used in the present invention. Extended duration may be obtained by selecting appropriate macromolecules, for example, polyesters, polyamino acids, polyvinylpyrrolidone, ethylenevinyl acetate, methylcellulose, carboxymethylcellulose, or protamine sulfate, and by selecting the concentration of macromolecules, as well as the methods of incorporation, in order to prolong release. Another possible method to extend the duration of action by controlled release preparations is to incorporate an active compound used in the present invention into particles of a polymeric material such as polyesters, polyamino acids, hydrogels, poly (lactic acid) or ethylene vinylacetate copolymers. Alternatively, instead of incorporating a compound into these polymeric particles, it is possible to entrap a compound used in the present invention in microcapsules prepared, for example, by coacervation techniques or by interfacial polymerization, for example, hydroxymethylcellulose or gelatin-microcapsules, respectively, or in colloidal drug delivery systems, for example, liposomes, albumin microspheres, microemulsions, nanoparticles, and nanocapsules, or in macroemulsions. Such teachings are disclosed in *Remington's Pharmaceutical Sciences* (1980).

A diagnosis of "myocardial infarction" is one involving medical judgment, and typically relies on a finding of at least two of the following symptoms and indications:

1) chest pain of at least 15 minute duration;
2) at least two values of serum creatine kinase and serum creatine kinase B at least two standard deviations above the normal range 10–16 h after onset of symptoms;
3) two or more serum lactate dehydrogenase levels that are at least two standard deviations above the normal range within 48–72 hours after onset of symptoms, including an isoenzyme pattern typical of myocardial infarction; and
4) development of new Q waves and/or initial ST elevation followed by T-wave inversion in at least two of the 12 standard ECG leads.

The acute phase of myocardial infarction occurs during the first 72 hours after the onset of the symptoms or indications described above. The treatment which is the subject of this invention is given during the acute phase of myocardial infarction, that is, in acute myocardial infarction.

A patient in need of the compounds used in the present invention is one who is in the acute phase of myocardial infarction, and who also is incapable of auto-regulation of blood glucose. A patient is incapable of auto-regulation if that patient: 1) was previously diagnosed with insulin-dependent diabetes (IDDM) or non-insulin dependent diabetes (NIDDM), according to the definitions of the National Diabetes Data Group [*Diabetes,* 28:1039–1057 (1979)]; 2) has a blood glucose level greater than 11 mmol/liter, even without a previous diagnosis of diabetes; or 3) has an abnormal glucose tolerance.

The dose of GLP-1, GLP-1 analog, or GLP-1 derivative effective to normalize a patient's blood glucose level will depend on a number of factors, among which are included, without limitation, the patient's sex, weight and age, the severity of inability to regulate blood glucose, the underlying causes of inability to regulate blood glucose, whether glucose, or another carbohydrate source, is simultaneously administered, the route of administration and bioavailability, the persistence in the body, the formulation, and the potency. Where administration is continuous, a suitable dosage rate is between 0.25 and 6 pmol/kg body weight/min, preferably from about 0.5 to about 1.2 pmol/kg/min. Where administration is intermittent, the dose per administration should take into account the interval between doses, the bioavailability of GLP-1, GLP-1 analog, or GLP-1 derivative, and the level needed to effect normal blood glucose. It is within the skill of the ordinary physician to titrate the dose and rate of administration of GLP-1, GLP-1 analog, or GLP-1 derivative to achieve the desired clinical result.

The present invention will be more readily understood by reference to specific examples, which are provided to illustrate, not to limit, the present invention.

EXAMPLE 1

GLP-1 (7-36) amide was administered by a subcutaneous infusion at a dose rate of 1.2 pmol/kg/hr, for ten hours during the night, to five patients having non-insulin dependent diabetes (NIDDM). As a control, insulin was continuously infused in the same five patients, but on a different day than the GLP-1 (7-36) amide infusion. The rate of insulin infusion was adjusted every two hours to achieve optimum control, and to avoid hypoglycemia. As demonstrated by the data in Table 1, and in FIG. 1, subcutaneous infusion of GLP-1 (7-36) amide nearly normalized blood glucose without inducing hypoglycemia in any of the patients. The metabolic control with GLP-1 (7-36) amide was better than that achieved by insulin, and the average blood glucose level was lower for GLP-1 (7-36) amide treatment than for the control by a statistically significant amount at 23:00, 0:00, and at 1:00.

TABLE 1

Average blood glucose levels for five NIDDM patients continuously infused for ten hours during the night with GLP-1 (7–36) amide. In a control study with the same patients on a different day, insulin was administered by continuous infusion.

| | GLP-1 Infusion | | Insulin Infusion (Control) | |
|---|---|---|---|---|
| Hour | Average Blood Glucose (mM) | Std. Error (mM) | Average Blood Glucose (mM) | Std. Error (mM) |
| 21:00 | 7.5 | 0.45 | 6.9 | 0.68 |
| 22:00 | 5.4 | 0.76 | 6.6 | 0.55 |
| 23:00 | 4.1 | 0.16 | 5.9 | 0.98 |
| 0:00 | 4.4 | 0.23 | 5.6 | 0.90 |
| 1:00 | 4.4 | 0.29 | 5.1 | 0.58 |
| 2:00 | 4.8 | 0.34 | 5.2 | 0.58 |
| 3:00 | 5.2 | 0.41 | 5.4 | 0.30 |
| 4:00 | 5.4 | 0.41 | 5.7 | 0.25 |
| 5:00 | 5.8 | 0.41 | 6.0 | 0.30 |
| 6:00 | 6.0 | 0.45 | 6.1 | 0.38 |
| 7:00 | 6.2 | 0.45 | 6.1 | 0.33 |

EXAMPLE 2

Figure 2:
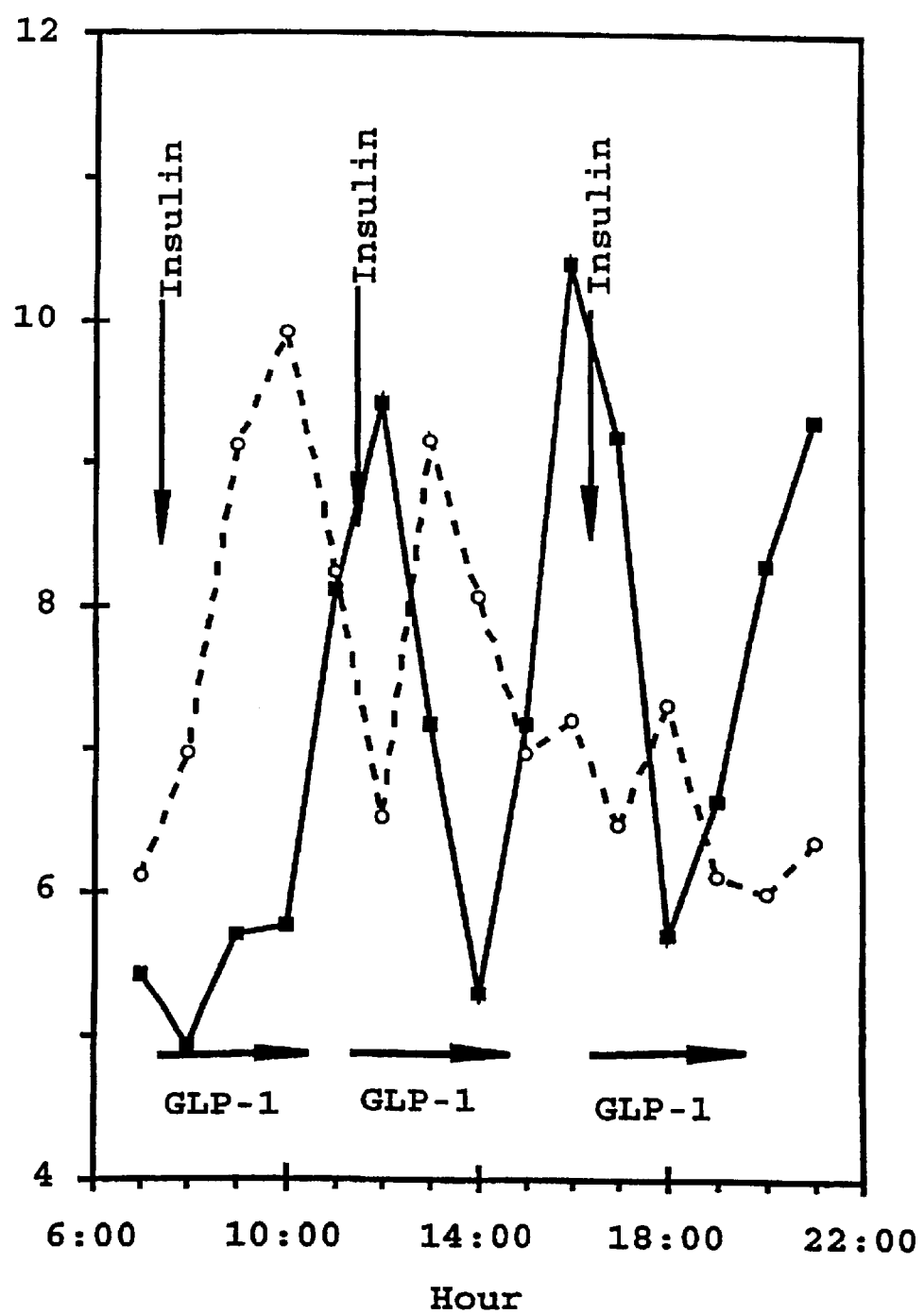
FIG. 2 is a graph showing the effect of GLP-1 (7-36) amide infusion on average blood glucose concentration (mM) —■— in five NIDDM patients when infused during the day, for three hours starting at the beginning of each of three meals. The graph also depicts the effect of subcutaneous injection of insulin on average blood glucose concentration --O-- in the same five NIDDM patients, but on a different day, and with injection shortly before each meal.

During the day, GLP-1 (7-36) amide was infused into five NIDDM patients for three hours during breakfast, lunch, and dinner. The infusion times were 7:30–10:30 (breakfast), 10:30–1:30 (lunch), and 4:30–7:30 (dinner), as indicated in FIG. 2. In a control experiment in the same five NIDDM patients conducted on a different day, insulin was injected subcutaneously just before the start of the meals, as indicated in FIG. 2. While GLP-1 was infused, the post-prandial glucose excursions observed with insulin injection were eliminated; and normal blood glucose levels were maintained. Immediately after terminating each GLP-1 (7-36) amide infusion, the blood glucose level increased significantly. No untoward side effects of GLP-1 (7-36) amide were observed. These data indicate that GLP-1 (7-36) amide infusion more effectively controls post-prandial glucose levels than insulin injection, and that the control is effective as long as GLP-1 (7-36) amide infusion is continued.

TABLE 2

Average blood glucose levels for five NIDDM patients infused with GLP-1 (7–36) amide for three hours, beginning at the start of each meal. In a control study with the same patients on a different day, insulin was administered by subcutaneous injection just before each meal. Meals began at 7:30, 10:30, and at 4:30.

| | GLP-1 Infusion | | Insulin Subcutaneous Injection | |
|---|---|---|---|---|
| Hour | Average Blood Glucose (mM) | Std. Error (mM) | Average Blood Glucose (mM) | Std. Error (mM) |
| 7:00 | 5.4 | 0.35 | 6.1 | 0.41 |
| 8:00 | 4.9 | 0.38 | 7.0 | 0.51 |
| 9:00 | 5.7 | 0.59 | 9.1 | 0.74 |
| 10:00 | 5.8 | 1.06 | 9.9 | 0.78 |
| 11:00 | 8.1 | 0.94 | 8.2 | 0.76 |
| 12:00 | 9.4 | 0.59 | 6.5 | 0.74 |
| 13:00 | 7.2 | 1.18 | 9.1 | 0.90 |
| 14:00 | 5.3 | 1.21 | 8.1 | 0.91 |
| 15:00 | 7.2 | 0.71 | 7.0 | 0.87 |
| 16:00 | 10.4 | 0.26 | 7.2 | 0.57 |
| 17:00 | 9.2 | 1.06 | 6.5 | 0.59 |
| 18:00 | 5.7 | 1.59 | 7.3 | 0.65 |
| 19:00 | 6.6 | 0.94 | 6.1 | 0.59 |
| 20:00 | 8.3 | 0.71 | 6.0 | 0.41 |
| 21:00 | 9.3 | 0.71 | 6.4 | 0.44 |

I claim:

1. A method of reducing mortality and morbidity after myocardial infraction, comprising administering to a patient in need thereof, a compound selected from the group consisting of GLP-1, GLP-1 analogs, GLP-1 derivatives and pharmaceutically-acceptable salts thereof, at a dose effective to normalize blood glucose.

2. The method of claim 1, wherein the compound is administered intravenously.

3. The method of claim 2, wherein the administration is continuous.

4. The method of claim 3 wherein the rate of administration of the compound is between 0.25 and 6 pmol/kg/min.

5. The method of claim 4 wherein the rate of administration of the compound is between 0.5 and 2.4 pmol/kg/min.

6. The method of claim 4 wherein said rate is between about 0.5 and about 1.2 pmol/kg/min.

7. The method of claim 2 wherein the intravenous administration is intermittent.

8. The method of claim 2 wherein the compound is administered intravenously and also administered by another parenteral route.

9. The method of claim 8 wherein the other parenteral route is the subcutaneous route.

10. The method of claim 1, wherein the compound is administered subcutaneously.

11. The method of claim 3, wherein the administration is continuous.

12. The method of claim 1 wherein the compound administered is GLP(7-36) amide, or a pharmaceutically-acceptable salt thereof.

13. A method of reducing mortality and morbidity after myocardial infraction, comprising administering a GLP-1 analog to a patient in need thereof at a dose effective to normalize blood glucose, said GLP-1 analog being represented by the following structural formula:

$R_1$—X—Glu—Gly—Thr—Phe—Thr—Ser—Asp—Val—Ser—Ser—Tyr—Leu—Y—Gly—Gln—Ala—Ala—Lys—Z—Phe—Ile—Ala—Trp—Leu—Val—Lys—Gly—Arg—$R_2$ and pharmaceutically-acceptable salts thereof, wherein:

$R_1$ is selected from the group consisting of L-histidine, D-histidine, desamino-histidine, 2-amino-histidine, β-hydroxy-histidine, homohistidine, alpha-fluoromethyl-histidine, and alpha-methyl-histidine;

X is selected from the group consisting of Ala, Gly, Val, Thr, Ile, and alpha-methyl-Ala;

Y is selected from the group consisting of Glu, Gin, Ala, Thr, Ser, and Gly;

Z is selected from the group consisting of Glu, Gln, Ala, Thr, Ser, and Gly;

$R_2$ is selected from the group consisting of $NH_2$, and Gly—OH;

provided that the GLP-1 analog has an isoelectric point in the range from about 6.0 to about 9.0 and further providing that when $R_1$ is His, X is Ala, Y is Glu, and Z is Glu, $R_2$ must be $NH_2$.

14. A method of reducing mortality and morbidity after myocardial infraction in a patient with non-insulin dependent diabetes, said method comprising the step of administering to the patient, at a dose effective to normalize blood glucose, a compound selected from the group consisting of GLP-1, GLP-1 analogs, GLP-1 derivatives and pharmaceutically-acceptable salts thereof.

15. A method of reducing mortality and morbidity after myocardial infraction in a patient with non-insulin dependent diabetes, said method comprising the step of administering to the patient, at a dose effective to normalize blood glucose, a GLP-1 analog represented by the following structural formula:

$R_1$—X—Glu—Gly—Thr—Phe—Thr—Ser—Asp—Val—Ser—Ser—Tyr—Leu—Y—Gly—Gln—Ala—Ala—Lys—Z—Phe—Ile—Ala—Trp—Leu—Val—Lys—Gly—Arg—$R_2$ and pharmaceutically-acceptable salts thereof, wherein:

$R_1$ is selected from the group consisting of L-histidine, D-histidine, desamino-histidine, 2-amino-histidine, β-hydroxy-histidine, homohistidine, alpha-fluoromethyl-histidine, and alpha-methyl-histidine;

X is selected from the group consisting of Ala, Gly, Val, Thr, Ile, and alpha-methyl-Ala;

Y is selected from the group consisting of Glu, Gin, Ala, Thr, Ser, and Gly;

Z is selected from the group consisting of Glu, Gln, Ala, Thr, Ser, and Gly;

$R_2$ is selected from the group consisting of $NH_2$, and Gly—OH;

provided that the GLP-1 analog has an isoelectric point in the range from about 6.0 to about 9.0 and further providing that when $R_1$ is His, X is Ala, Y is Glu, and Z is Glu, $R_2$ must be $NH_2$.

16. A method of reducing mortality and morbidity after myocardial infraction in a patient having a blood glucose level greater than 11 mmole/liter, said method comprising the step of administering to the patient, at a dose effective to normalize blood glucose, a compound selected from the group consisting of GLP-1, GLP-1 analogs, GLP-1 derivatives and pharmaceutically-acceptable salts thereof.

17. A method of reducing mortality and morbidity after myocardial infraction in a patient having a blood glucose level greater than 11 mmole/liter, said method comprising the step of administering to the patient, at a dose effective to normalize blood glucose, a GLP-1 analog represented by the following structural formula:

$R_1$—X—Glu—Gly—Thr—Phe—Thr—Ser—Asp—Val—Ser—Ser—Tyr—Leu—Y—Gly—Gln—Ala—Ala—Lys—Z—Phe—Ile—Ala—Trp—Leu—Val—Lys—Gly—Arg—$R_2$ and pharmaceutically-acceptable salts thereof,
wherein:
$R_1$ is selected from the group consisting of L-histidine, D-histidine, desamino-histidine, 2-amino-histidine, β-hydroxy-histidine, homohistidine, alpha-fluoromethyl-histidine, and alpha-methyl-histidine;
X is selected from the group consisting of Ala, Gly, Val, Thr, Ile, and alpha-methyl-Ala;
Y is selected from the group consisting of Glu, Gln, Ala, Thr, Ser, and Gly;
Z is selected from the group consisting of Glu, Gln, Ala, Thr, Ser, and Gly;
$R_2$ is selected from the group consisting of $NH_2$, and Gly—OH;
provided that the GLP-1 analog has an isoelectric point in the range from about 6.0 to about 9.0 and further providing that when $R_1$ is His, X is Ala, Y is Glu, and Z is Glu, $R_2$ must be $NH_2$.

18. A method of reducing mortality and morbidity after myocardial infraction in a patient with abnormal glucose tolerance, said method comprising the step of administering to the patient, at a dose effective to normalize blood glucose, a compound selected from the group consisting of GLP-1, GLP-1 analogs, GLP-1 derivatives and pharmaceutically-acceptable salts thereof.

19. A method of reducing mortality and morbidity after myocardial infraction in a patient having abnormal glucose tolerance, said method comprising the step of a GLP-1 analog to the patient, at a dose effective to normalize blood glucose, a GLP-1 analog represented by the following structural formula:

$R_1$—X—Glu—Gly—Thr—Phe—Thr—Ser—Asp—Val—Ser—Ser—Tyr—Leu—Y—Gly—Gln—Ala—Ala—Lys—Z—Phe—Ile—Ala—Trp—Leu—Val—Lys—Gly—Arg—$R_2$ and pharmaceutically-acceptable salts thereof,
wherein:
$R_1$ is selected from the group consisting of L-histidine, D-histidine, desamino-histidine, 2-amino-histidine, β-hydroxy-histidine, homohistidine, alpha-fluoromethyl-histidine, and alpha-methyl-histidine;
X is selected from the group consisting of Ala, Gly, Val, Thr, Ile, and alpha-methyl-Ala;
Y is selected from the group consisting of Glu, Gln, Ala, Thr, Ser, and Gly;
Z is selected from the group consisting of Glu, Gln, Ala, Thr, Ser, and Gly;
$R_2$ is selected from the group consisting of $NH_2$, and Gly—OH;
provided that the GLP-1 analog has an isoelectric point in the range from about 6.0 to about 9.0 and further providing that when $R_1$ is His, X is Ala, Y is Glu, and Z is Glu, $R_2$ must be $NH_2$.

* * * * *

UNITED STATES PATENT AND TRADEMARK OFFICE
CERTIFICATE OF CORRECTION

PATENT NO.    : 6,277,819 B1
DATED         : August 21, 2001
INVENTOR(S)   : Suad Efendic It is certified that error appears in the above-identified patent and that said Letters Patent is hereby corrected as shown below:

Column 18,
Lines 21 and 57, under "Y is selected" replace "Gin" with -- Gln --

Column 20,
Lines 6-11, first paragraph should read as:
-- A method of reducing mortality and morbidity after myocardial infarction in a patient having abnormal glucose tolerance, said method comprising the step of administering a GLP-1 analog to the patient, at a dose effective to normalize blood glucose, said GLP-1 analog represented by the following structural formula: --

Signed and Sealed this

Thirteenth Day of May, 2003

JAMES E. ROGAN
*Director of the United States Patent and Trademark Office*

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
      (A) LENGTH: 31 amino acids
      (B) TYPE: amino acid
      (C) STRANDEDNESS:
      (D) TOPOLOGY: linear (ii) MOLECULE TYPE: peptide (xi) SEQUENCE DESCRIPTION: SEQ ID NO: 1:

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
                20                  25                  30

(2) INFORMATION FOR SEQ ID NO: 2:

(i) SEQUENCE CHARACTERISTICS:
        (A) LENGTH: 31 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 2:

Xaa Xaa Glu Gly Thr Phe Thr Ser Asp Val Ser Ser Tyr Leu Xaa Gly
1               5                   10                  15

Gln Ala Ala Lys Xaa Phe Ile Ala Trp Leu Val Lys Gly Arg Xaa
                20                  25                  30

(2) INFORMATION FOR SEQ ID NO: 3:

(i) SEQUENCE CHARACTERISTICS:
        (A) LENGTH: 28 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 3:

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Xaa
                20                  25

(2) INFORMATION FOR SEQ ID NO: 4:

(i) SEQUENCE CHARACTERISTICS:
        (A) LENGTH: 30 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 4:

Ala Glu Gly Thr Phe Thr Ser Asp Val Ser Ser Tyr Leu Glu Gly Gln
1               5                   10                  15

Ala Ala Xaa Glu Phe Ile Ala Trp Leu Val Lys Gly Arg Xaa
                20                  25                  30

(2) INFORMATION FOR SEQ ID NO: 5:

(i) SEQUENCE CHARACTERISTICS:
        (A) LENGTH: 30 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 5:

His Ala Glu Gly Thr Phe Thr Ser Asp Val Ser Ser Tyr Leu Glu Gly

-continued

```
1               5               10              15
Gln Ala Ala Lys Glu Phe Ile Ala Trp Leu Val Lys Gly Arg
                20              25              30
```

(2) INFORMATION FOR SEQ ID NO: 6:

(i) SEQUENCE CHARACTERISTICS:
       (A) LENGTH: 4 amino acids
       (B) TYPE: amino acid
       (C) STRANDEDNESS:
       (D) TOPOLOGY: linear (ii) MOLECULE TYPE: peptide (xi) SEQUENCE DESCRIPTION: SEQ ID NO: 6:

Ser Arg Arg Gln